United States Patent [19]

Olsson et al.

[11] Patent Number: 5,034,390
[45] Date of Patent: Jul. 23, 1991

[54] PYRIDYL-AND PYRMIDYL-PIPERAZINES USEFUL FOR THE TREATMENT OF MENTAL DISORDERS

[75] Inventors: Knut G. Olsson, Malmö; Aina L. Abramo, Bjärred; Erik T. Lundstedt, Löddeköpinge; Curt Nordvi, Malmö0 all of Sweden

[73] Assignee: Pharmacia AB, Uppsala, Sweden

[21] Appl. No.: 414,114

[22] Filed: Sep. 28, 1989

[30] Foreign Application Priority Data

Sep. 28, 1988 [SE] Sweden .................................. 8803429

[51] Int. Cl.$^5$ .................. A61K 31/495; C07D 401/04; C07D 403/04
[52] U.S. Cl. .................................... 514/252; 514/212; 514/218; 514/235.8; 540/575; 540/598; 544/121; 544/295; 544/332; 544/360; 544/364; 544/365
[58] Field of Search ............... 544/295, 360, 364, 365, 544/332, 121; 540/575, 598; 514/212, 218, 235.8, 252

[56] References Cited

U.S. PATENT DOCUMENTS

| | | | |
|---|---|---|---|
| 2,979,508 | 4/1961 | Janssen | 544/360 |
| 4,191,765 | 3/1980 | Fritsch et al. | 544/360 |
| 4,704,390 | 11/1987 | Caprathe et al. | 544/360 |
| 4,748,240 | 5/1988 | Stack et al. | 544/360 |
| 4,873,331 | 10/1989 | Childers, Jr. et al. | 544/360 |
| 4,892,943 | 1/1990 | Abou-Gharbia | 544/360 |

FOREIGN PATENT DOCUMENTS 279598 8/1988 European Pat. Off.
890961 8/1989 World Int. Prop. O.

OTHER PUBLICATIONS

Nakao et al., Chem. 109–231070h (1988).
Jaen, et al., Chem. Abst. 109-54737h (1988).
Lowe et al, Chem. Abst., 110-8234q (1989).
Noritsina et al., Chem. Abst., 111-173259r (1989).
Macallum et al, Chem. Abst. 112-48593d (1970).
Tomino et al, Chem. Abst. 112-55583d (1990).
Saito et al., Chem. Abst., 112-70036w (1990).

*Primary Examiner*—Cecilia Shen
*Attorney, Agent, or Firm*—Scully, Scott, Murphy and Presser

[57] ABSTRACT

The present invention concerns novel compounds of the general formula;

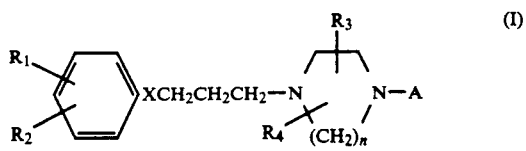

wherein $R_1$ is halogen or hydrogen and $R_2$ is halogen;
X is either oxygen, sulfor or methylene
$R_3$ and $R_4$ are the same or different and selected from hydrogen and lower alkyl;
n is 2 or 3;
A is selected from the following pyrimidyl or pyridyl groups

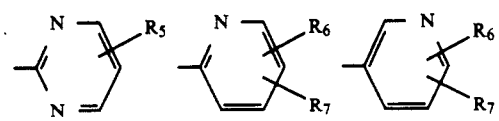

wherein $R_5$ is selected from hydrogen, lower alkyl or halogen;
$R_6$ and $R_7$ are the same or different and selected from hydrogen, halogen, lower alkyl, electron donor groups such as lower alkoxy or hydroxy, electron acceptor groups such as cyano, nitro, trifluoromethyl, $COOR_8$, $CONR_9R_{10}$ or CO-B;
wherein $R_8$ is hydrogen or lower alkyl;
$R_9$ and $R_{10}$ are the same or different and selected from hydrogen, lower alkyl and cycloalkyl;
B is selected from

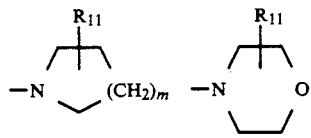

wherein m is 1, 2, 3 or 4.
$R_{11}$ is selected from hydrogen or lower alkyl, and the pharmacologically active salts thereof.

The new compounds are useful for treating mental disorders.

16 Claims, No Drawings

PYRIDYL- AND PYRMIDYL-PIPERAZINES USEFUL FOR THE TREATMENT OF MENTAL DISORDERS

BACKGROUND

There is an urgent need for efficient drugs in the treatment of mental disorders which are more effective and which have fewer side effects than the drugs in clinical use today. Antipsychotic drugs in current use produce a range of troublesome extrapyramidal movement disorders (e.g. acute dystonic reactions and tardive dyskinesia) and are poor in ameliorating the negative symptoms (e.g. restricted or blunted emotional arousal) of schizophrenia. The main disadvantage of the antidepressants is that they fail to alleviate depression in 30 to 40% of patients. Anxiolytics are commonly associated with addictive properties.

PRIOR ART

Various pyridyl- and pyrimidyl-piperazine derivatives pharmacologically active in the central nervous system are known in the art. Some representative examples can be mentioned. Azaperone, a neuroleptic drug of the butyrophenone series, is a sedative for pigs. Buspirone is an anxiolytic. The anxiolytic effect is thought to be mediated via effects on the 5HT-receptors.

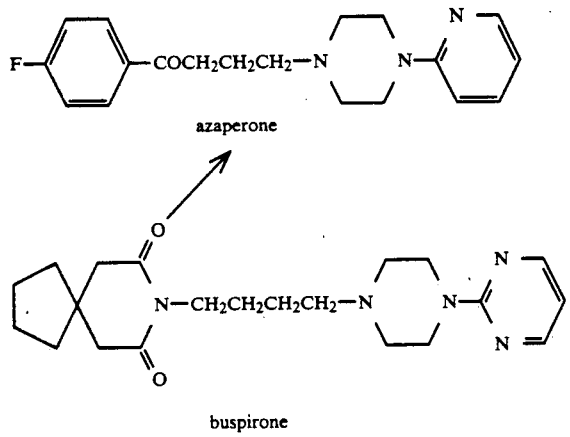

azaperone buspirone

DESCRIPTION OF THE INVENTION

Pyridyl- and pyrimidyl-piperazines substituted in the 4-position of the piperazine ring with a phenyl-butyl or phenoxypropyl group have unexpectedly been found to exhibit pharmacological properties superior to compounds known in the art.

According to the invention there are provided novel compounds having the general formula (I).

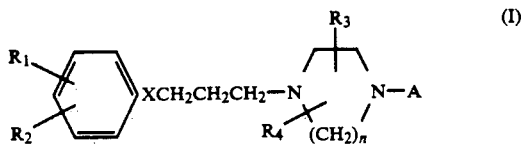

wherein $R_1$ is halogen or hydrogen and $R_2$ is halogen;
wherein X is either oxygen, a sulfor or a methylene;
$R_3$ and $R_4$ are the same or different and selected from hydrogen and lower alkyl;
n is 2 or 3;

A is selected from the following pyrimidyl or pyridyl groups

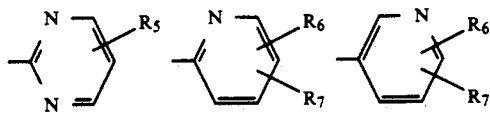

wherein $R_5$ is selected from hydrogen, lower alkyl or halogen;
$R_6$ and $R_7$ are the same or different and selected from hydrogen, halogen, lower alkyl, electron donor groups such as lower alkoxy or hydroxy, electron acceptor groups such as cyano, nitro, trifluoromethyl, $COOR_8$, $CONR_9R_{10}$ or CO-B;
wherein $R_8$ is hydrogen or lower alkyl;
$R_9$ and $R_{10}$ are the same or different and selected from hydrogen, lower alkyl and cycloalkyl;
B is selected from

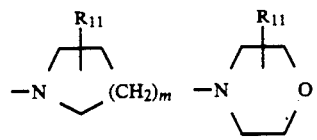

wherein m is 1, 2, 3 or 4.
$R_{11}$ is selected from hydrogen or lower alkyl, and the pharmacologically active salts thereof, and when used in the foregoing definitions the term lower alkyl is meant to include straight and branched, saturated hydrocarbon groups having from 1 to 5 carbon atoms;
the term cycloalkyl is meant to include cyclic hydrocarbon groups having from 3 to 8 carbon atoms;
the term lower alkoxy is meant to include straight or branched, saturated hydrocarbon groups having from 1 to 5 carbon atoms;
the term halogen is meant to include fluoro, chloro and bromo.

It is preferred that $R_1$ is hydrogen and $R_2$ is halogen, fluoro is preferred.

As regards $R_3$ and $R_4$ hydrogen or methyl are preferred, especially hydrogen.

As regards $R_5$ hydrogen, alkyl or halogen, especially fluoro, is preferred.

As regards $R_6$ hydrogen, alkyl, alkoxy, amide, nitro, carboxy, trifluoromethyl, halogen, hydroxy or cyano is preferred.

It is preferred that $R_7$ is hydrogen, alkyl, alkoxy, nitro, carboxy, halogen, hydroxy, cyano or an amide group.

Compounds wherein A is 2-substituted pyridyl are of special interest, especially those carrying an alkoxy, hydroxy, alkyl, amide, cyano or hydrogen substituent in the 3-position.

The compounds of formula (I) have basic properties and, consequently, they may be converted to their therapeutically active acid addition salts by treatment with acid, or organic acids such as acetic, propanoic, glycolic, lactic, malonic, oxalic, succinic, fumaric, tartaric, citric and pamoic acid.

Conversely, the salt form can be converted into the free base form by treatment with alkali.

The compounds of formula (I) and their pharmaceutically acceptable salts have valuable pharmacological properties, making them useful for the treatment of mental disorders such as psychoses, depression and anxiety. Stress and anxiety in animals can also be treated. The compounds of the present invention show psychotropic properties. For example, they show affinity for 5-HT$_2$ and D$_2$ binding sites in the brain. In behavioural test models the compounds show a limbic profile of action, i.e. they show potent effects in tests for exploratory behaviour, e.g. the staircase test.

Compounds with a combined 5-HT$_2$/D$_2$ affinity, e.g. clozapine, have antipsychotic effect with a low degree of extrapyramidal side-effects. Furthermore, compounds with affinity for 5-HT$_2$ binding sites has been found to affect depressive illness as well as anxiety states.

Effective quantities of any of the foregoing pharmacologically active compounds of formula (I) may be administered to a human being or an animal for therapeutic purposes according to usual routes of administration and in usual forms, such as orally in solutions, emulsions, suspensions, pills, tablets and capsules, in pharmaceutically acceptable carriers and parenterally in the form of sterile solutions. For the parenteral adminstration of the active substance the carrier of excipient may be a sterile, parenterally acceptable liquid, e.g. water, or a parenterally acceptable oil, e.g. arachidic oil.

Although very small quantities of the active materials of the present invention are effective when minor therapy is involved or in the cases of administration to subjects having a relatively low body weight, unit dosages are usually from 2 milligrams upwards, preferably 10, 25 or 50 milligrams or even higher depending on the condition to be treated and the age and weight of the patients as well as the response to the medication.

The unit dose may be from 0.1 to 100 milligrams, preferably from 10 to 50 milligrams. Daily dosages should preferably range from 10 milligrams to 200 milligrams. The exact individual dosages as well as daily dosages will, of course, be determined according to standard medical principles under the direction of a physician or veterinarian.

METHODS OF PREPARATION

The compounds having the general formula (I) may be prepared by conventional methods.

Method 1

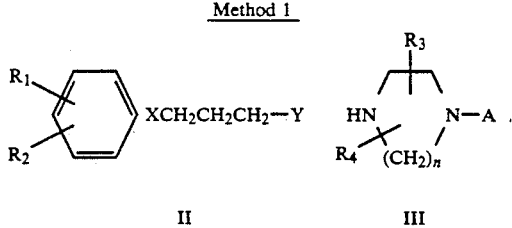

II            III

A compound of formula (II), wherein R$_1$, R$_2$ and X are as previously defined and Y is a suitable leaving group such as halogen and alkyl- or arylsulfonate is reacted with a compound of formula (III) wherein R$_3$, R$_4$, A and n are as defined previously. The reactions may be carried out using standard N-alkylating procedures.

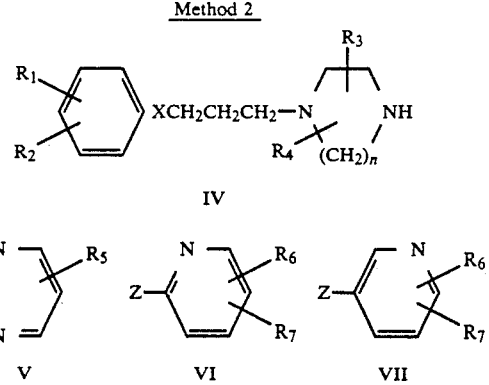

A compound of formula (IV), wherein R$_1$, R$_2$, R$_3$, R$_4$, X and n are as previously defined is reacted with a compound of formula (V), (VI) or (VII), wherein R$_5$, R$_6$ and R$_7$ are as previously defined and Z is a leaving group, e.g. halogen.

Examples

The following examples are intended to illustrate but not to limit the scope of the invention, although the compounds named are of particular interest for out intended purposes. These compounds have been designated by a number code, a:b, where a means the number of the example, wherein the preparation of the compound in question is described, and b refers to the order of the compounds prepared according to that example. Thus, compound 1:2 means the second compound prepared according to Example 1.

The structures of the compound are confirmed by NMR, masspectra and elementary analysis. When melting points are given, these are uncorrected.

EXAMPLE 1

4-/4-(p-fluorophenyl)butyl/-1-(2-pyridyl)piperazine fumarate 6.0 g (0.0323 mol) of 4(p-fluorophenyl)butylchloride, 5.3 g (0.0323 mol) of pyridylpiperazine, 5.2 g of sodiumcarbonate and 0.1 g of iodide was heated together with 25 ml of xylene at 150° C. (temperature of oil bath) for 20 h.

After cooling the reaction mixture to ~100° C., 50 ml of toluene was added and the mixture was filtered. 25 ml of ether was added to the filtrate. The organic solution was washed three times with 25 ml of water and finally once with 25 ml of a saturated sodiumchloride solution.

Evaporation of the solvents yielded crude base which was crystallized by cyclohexane. The melting point obtained for the free base is 57°-58° C.

The free base was then dissolved in ethanol/ether and the fumarate was precipitated with excess of fumaric acid in ethanol. Recrystallization from ethanol yielded 4.8 g of the title compound (1:1), m.p. 160°-161° C.

EXAMPLE 2

4-/4-(p-fluorophenyl)butyl/-1-/2-(3-carbamylpyridyl)-/piperazine dihydrochloride 5.9 g (0.025 mol) of 1-/4-(p-fluorophenyl)butyl/piperazine, 3.9 g (0.025 mol) of 2-chloronicotinic acid amide and 3.1 g of sodiumcarbonate was refluxed together with 20 ml of toluene for 20 h.

After cooling a solid mixture was obtained which ws dissolved by ethylacetate and water. The toluene/ethylacetate phase was separated and then washed with water and sodiumchloride solution and was then dried with sodiumsulfate.

Evaporation of the solvents yielded the crude free base, which was recrystallized from toluene. The free base obtained melted at 135°-136° C.

5 g of the free base was dissolved in ethanol and the dihydrochloride was precipated by excess of hydrochloric acid in ethanol. Recrystallization yielded 3.0 g of the titled compound (2:1), m.p. 210°-213° C.

Using essentially the same procedure the following compounds are prepared (isolated and purified by Flashchromatography as the pure base or as the corresponding salts) from the corresponding starting material.

2:2  4-/3(p-fluorophenoxy)propyl/-1-/6-chloro-2-pyridyl/piperazine hydrochloride, m.p. 185°-186° C.

2:3  4-/3-(p-fluorophenoxy)propyl/-1-/2-pyrimidyl/piperazine hydrochloride hemihydrate, m.p. 208°-210° C.

2:4  4-/3-(p-fluorophenoxy)propyl/-1-/2-pryridyl/piperazine dihydrochloride, m.p. 233°-235° C.

2:5  4-/3-(p-fluorophenoxy)propyl/-1-/3-carbamyl-2-pyridyl/piperazine dihydrochloride, m.p. 240°-242° C.

2:6  4-/4-(p-fluorophenyl)butyl/-1-/2-pyrimidyl/piperazine hydrochloride, m.p. 197°-198° C.

2:7  4-/4-(p-fluorophenyl)butyl/-1-/2-pyridyl/piperazine fumarate, m.p. 160°-161° C.

2:8  4-/3-(p-fluorophenoxy)propyl/-1-/3-nitro-2-pyridyl/piperazine hydrochloride, m.p. 182°-183° C.

2:9  4-/4-(p-fluorophenyl)butyl/-1-/6-chloro-2-pyridyl/-piperazine hydrochloride, m.p. 150°-151° C.

2:10  4-/3-(p-fluorophenoxy)propyl/-1-/6-methoxy-2-pyridyl/piperazine fumarate, m.p. 185°-186° C.

2:11  4-/3-(p-fluorophenoxyl)propyl/-1-/3-carbamyl-2-pyridyl/-/1,4-diazacycloheptane/oxalate, m.p. 148°-150° C. (base m.p. 140°-141° C.)

2:12  4-/4-(p-fluorophenyl)butyl/-1-/3-ethoxy-2-pyridyl/piperazine dihydrochloride, hemiisopropanol hemihydrate, m.p. 168°-169° C.

2:13  4-/3-(p-fluorophenoxy)propyl/-1-(3-carbamyl-2-pyridyl) 2,5-transdimethylpiperazine 1,5 fumarate, m.p. 172°-173° C. (base m.p. 115ᵈ-116° C.)

2:14  4-/4-(p-fluorophenyl)butyl/-1-/6-methyl-2-pyridyl/piperazine fumarate, m.p. 172°-173° C.

2:15  4-/3-(3,4-difluorophenoxy)propyl/-1-/6-methyl-2-pyridyl/piperazine dihydrochloride, d. 230° C.

2:16  4-/3-(3,4-difluorophenoxy)propyl/-1-/3-(N-methyl-carbamyl)-2-pyridyl/piperazine 1,5 hydrochloride, m.p. 211°-213° C.

2:17  4-/3-(p-fluorophenoxy)propyl/-1-/3-hydroxy-2-pyridyl/piperazine dihydrochloride, m.p. 240° C. (base m.p. 105° C.)

2:18  4-/3-(p-fluorophenoxy)propyl/-1-/3-trifluoromethyl-6-chloro-2-pyridyl/piperazine hydrochloride, m.p. 190° C.

2:19  4-/3-(p-fluorothiophenoxy)propyl/-1-/3-carbamyl-2-pyridyl/piperazine dihydrochloride, m.p. 205° C.

2:20  4-/3-(p-fluorophiophenoxyl)propyl/-1-2-pyridyl/piperazine dihydrochloride, m.p. 150° C.

2:21  4-/3-(p-fluorophenoxyl)propyl/-1-/5-morpholinocarbonyl-2-pyridyl/piperazine 2:22  4-/4-(p-fluorophenyl)butyl/-1-/3-piperidinocarbonyl-2-pyridyl/piperazine

EXAMPLE 3

Affinity to 5-HT₂ receptors

The binding assay is carried out essentially as described by Leysen et al. (Mol. Pharmacol. 21, 301-14, 1982) using $^3$H-ketanserine as ligand.

TABLE 1

| Compound | $K_i$ (nM) |
|---|---|
| 2:9 | 7 |
| 2:10 | 11 |
| 2:19 | 7 |

The compounds listed in Table 1 are not given for purpose of limiting the invention thereto but only to exemplify the useful pharmacological activities of compounds within the scope of formula (I).

EXAMPLE 4

The following formulations are representative for all of the pharmacologically active compounds of this invention. Example of a suitable capsule formulation:

|  | Per capsule, mg |
|---|---|
| Active ingredient, as salt | 10 |
| Lactose | 250 |
| Starch | 120 |
| Magnesium stearate | 5 |
| Total | 385 |

In case of higher amounts of active ingredients, the amount of lactose used may be reduced.

Example of a suitable tablet formulation:

|  | Per tablet, mg |
|---|---|
| Active ingredient, as salt | 10 |
| Potato starch | 90 |
| Colloidal Silica | 10 |
| Talc | 20 |
| Magnesium stearate | 2 |
| 5% aqueous solution of gelatin | 25 |
| Total | 157 |

Solutions for parenteral applications by injection can be prepared in a aqueous solution of a water-soluble pharmaceutically acceptable salt of the active substance preferably in a concentration of from about 0.5% to about 5% by weight. These solutions may also contain stabilizing agents and/or buffering agents and may conveniently be provided in various dosage unit ampoules.

We claim:

1. Compounds having the formula (I)

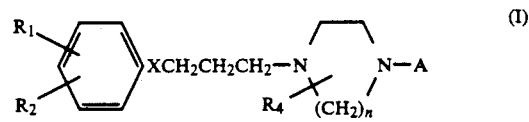

or pharmaceutically acceptable salts thereof wherein
$R_1$ is halogen, or hydrogen and
$R_2$ is halogen;
X is either oxygen, sulfur or methylene;
$R_3$ and $R_4$ are the same or different and selected from the group consisting of hydrogen and lower alkyl;
n is 2 or 3;

A is selected from the group consisting of pyrimidyl and pyridyl groups having the formula:

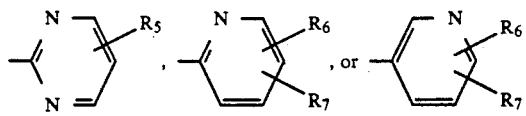

wherein $R_5$ is selected from the group consisting of hydrogen, lower alkyl and halogen;

$R_6$ and $R_7$ are the same or different and selected from the group consisting of hydrogen, halogen, lower alkyl, electron donor groups selected from the group consisting of lower alkoxy and hydroxy, and electron acceptor groups selected from the group consisting of cyano, nitro, trifluoromethyl, $COOR_8$, $CONR_9R_{10}$ and CO-B; wherein $R_8$ is hydrogen or lower alkyl;

$R_9$ and $R_{10}$ are the same or different and selected from the group consisting of hydrogen, lower alkyl and cycloalkyl;

B is

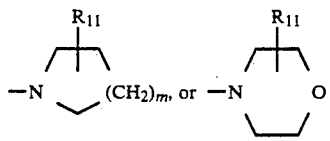

wherein m is 1, 2, 3 or 4, and $R_{11}$ is selected from the group consisting of hydrogen and lower alkyl.

2. Compounds according to claim 1 wherein $R_1$ is hydrogen and $R_2$ is halogen.

3. Compounds according to claim 1 or 2 wherein n=2.

4. Compounds according to claim 1 or 2, wherein $R_3$ and $R_4$ are hydrogen or methyl, 5. Compounds according to claim 1 or claim 2, wherein A is

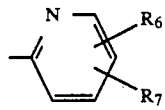

6. Compounds according to claim 4, wherein $R_6$ is hydrogen, alkyl, trifluoromethyl, alkoxy, amide, hydroxy, carboxy, nitro or cyano and $R_7$ is hydrogen, alkyl, alkoxy, hydroxy, nitro, halogen, carboxy, cyano or an amide group.

7. Compounds according to 6 wherein X is oxygen or methylen.

8. Compounds according to claim 5, wherein $R_6$ is hydrogen, alkyl, or trifluoromethyl and $R_7$ is alkoxy, hydrogen, hydroxy, carboxy, nitro, halogen, cyano or an amide group and $R_7$ is situated in the 3-position.

9. Compounds according to 1 wherein X is oxygen.

10. Compounds according to claim 6, wherein $R_6$ is hydrogen and $R_7$ is hydrogen, cyano, nitro, alkoxy, alkyl, hydroxy or an amide substituent.

11. Compounds according to claim 7 wherein $R_7$ is an amide, hydroxy, hydrogen, methyl, cyano or methoxy substituent.

12. Compounds according to claim 1 wherein $R_1$ is hydrogen and $R_2$ is fluoro.

13. Compounds according to claims 1 or 2 wherein $R_3$ and $R_4$ are hydrogen.

14. A pharmaceutical composition for the treatment of mental disorders selected from the group consisting of psychosis, depression and anxiety which comprises a pharmaceutically effective amount of a compound according to claim 1 and a pharmaceutically acceptable carrier therefor.

15. A method of treating a host affected with a mental disorder selected from the group consisting of psychosis, depression and anxiety which comprises administering to said host an effective amount of a compound according to claim 1.

16. Compounds according to claim 5 wherein n is 2.

* * * * *

UNITED STATES PATENT AND TRADEMARK OFFICE
CERTIFICATE OF CORRECTION

PATENT NO. : 5,034,390

DATED : July 23, 1991

INVENTOR(S) : Knut Gunnarr Olsson, et al.

It is certified that error appears in the above-identified patent and that said Letters Patent is hereby corrected as shown below:

Column 4, line 27: "out" should read as --our--

Column 5, line 18: "4-/3(p" should read as --4-/3-(p--

Column 5, line 39: "fluorophenoxyl" should read as --fluorophenoxy--

Column 5, line 63: "fluorophiophenoxyl" should read as --fluorothiophenoxyl--

Signed and Sealed this

Fifth Day of January, 1993

*Attest:*

DOUGLAS B. COMER

*Attesting Officer*   Acting Commissioner of Patents and Trademarks